United States Patent [19]
Sackler et al.

[11] Patent Number: 4,954,351
[45] Date of Patent: Sep. 4, 1990

[54] METHOD OF PRODUCING STANDARDIZED POVIDONE IODINE PREPARATIONS AND SUCH PREPARATIONS

[75] Inventors: Mortimer D. Sackler, Schattdorf; Ronald B. Miller, Basel, both of Switzerland; Erwig O. Pinter; Helmut E. W. Rackur, both of Limburg/Lahn, Fed. Rep. of Germany; Raymond R. Sackler; Richard S. Sackler, both of Greenwich, Conn.; Alfred Halpern, deceased, late of Great Neck, N.Y., by Marjorie A. Halpern, administratrix

[73] Assignee: Euroceltique S.A., Luxembourg

[21] Appl. No.: 247,876

[22] Filed: Sep. 22, 1988

Related U.S. Application Data

[63] Continuation of Ser. No. 927,841, Nov. 5, 1986, abandoned, which is a continuation-in-part of Ser. No. 802,322, Nov. 27, 1985, abandoned, which is a continuation of Ser. No. 585,428, Mar. 2, 1984, abandoned.

[30] Foreign Application Priority Data

Mar. 2, 1983 [DE] Fed. Rep. of Germany ....... 3307219
Apr. 15, 1983 [DE] Fed. Rep. of Germany ....... 3313655

[51] Int. Cl.$^5$ ............................................. A61K 33/36
[52] U.S. Cl. ....................................... 424/667; 424/80
[58] Field of Search .......................... 424/80, 150, 667

[56] References Cited

U.S. PATENT DOCUMENTS 4,271,149  6/1981  Winicov et al. ...................... 424/80

Primary Examiner—Allen J. Robinson
Assistant Examiner—Zohreh A. Fay
Attorney, Agent, or Firm—Steinberg & Raskin

[57] ABSTRACT

A pharmaceutical iodophor preparation having predictable microbicidal effectiveness and long duration of action comprising polyvinylpyrrolidone-iodine (PVPI), free iodine, a source of iodide ions and a source of iodate ions, the preparation having a ratio of available (titratable) iodine to iodide between 2:1 and 10:1, a pH between 5 and 6 and a free iodine concentration between 2 and 20 ppm, wherein the amount of iodate ion in the preparation is sufficient to maintain the free iodine concentration between 2 and 20 ppm for at least 12 months at 20° C.

9 Claims, No Drawings

METHOD OF PRODUCING STANDARDIZED POVIDONE IODINE PREPARATIONS AND SUCH PREPARATIONS

CROSS REFERENCE TO RELATED APPLICATIONS

This is a continuation of application Ser. No. 927,841, filed 11-5-86, now abandoned, which is a continuation-in-part of U.S. Pat. application Ser. No. 802,322, filed Nov. 27, 1985, now abandoned, which is itself a continuation of U.S. Pat. application Ser. No. 585,428, filed Mar. 2, 1984, now abandoned.

BACKGROUND OF THE INVENTION

This invention is concerned with a pharmaceutical iodophor preparation, its use and its manufacture. Apart from iodine with its longstanding disadvantages, iodophor preparations are known and commercially available which have considerable advantages over iodine, iodine tinctures etc. Attention is drawn, in particular, to polyvinylpyrrolidone iodine (PVP iodine), a preparation which is commercially available in a variety of forms and has recognizedly good microbicidal properties.

However, such iodophor preparations, including in particular PVP iodine, also have disadvantages which are important. These disadvantages relate primarily to the preparations' storage stability, their reliable effectiveness over an extended period and their reproducibility, i.e. their manufacture to a consistently good effective quality.

There has therefore been no shortage of formulations adapted to eliminate these disadvantages. For example, U.S. Pat. No. 4,113,857 proposes a process for manufacturing iodophor preparations, in which it is stressed that the preparation should not contain any iodide ion, this being based on the recognition that the presence of iodide ion should be regarded as a contamination leading to a reduction of the free, elementary, caustic iodine. According to this patent it is therefore important to produce iodophor preparations which are free of iodide ion.

Another method of improving iodophor preparations is described in U.S. Pat. No. 4,271,149. According to this patent preparations which are stable during storage are produced by the addition of iodate ion in an amount of 0.005% to 0.2%, preferably 0.05 to 0.1%, to the preparation and the control of the preparations' pH-value to within pH 5 to 7. In this patent great importance is attached to the iodide content required to achieve stability. This is illustrated by the results given in U.S. Pat. No. 4,271,149, especially for the preparations having a high iodide content. It is important to note that U.S. Pat. No. 4,271,149, does not distinguish between available iodine and free, equilibrium iodine, a distinction that, in pharmaceutical terms, is critical to the questions of efficacy and stability. Furthermore the preparations of Winicov have not proved to be sufficiently stable for pharmaceutical purposes.

From DE 27 18 385 a biocide substance is known, for example PVP iodine, for which the presence of an oxidizing agent is essential in order to oxidize iodide to yield free iodine, which is then directly complex-bound, whereby the oxidizing agent prevents the reforming of iodide from iodine up to a stable balance. This target is not achieved.

From DE 24 38 594 a disinfectant is known, which for instance contains PVP iodine, but which contains hydrogen peroxide as an essential additive; this leads to an essentially reduced iodine content, but not to a stable preparation.

In FR 745 693 a well known iodine bandage is described for which component ratios do not matter at all.

From the GB 2 024 012A a medical dressing is known which when applied to a wound gives off gaseous oxygen based on a concentration of a peroxide and decomposing agent suitable for it, for instance potassium iodide. Such a dressing has no relevance to the present invention.

In U.S. Pat. No. 4,125,602 a process for manufacturing an iodophor is described which aims at an economical and quick cycle of operations. The process produces a granulate with uniform particle size. This publication does not contain any suggestions as to how the disadvantages of PVP-iodine preparations can be avoided.

From U.S. Pat. No. 4,113,857 iodophors such as PVP iodine are known, in which iodide ions are considered disadvantageous. The aim is to produce iodide-free preparations which are not contaminated by iodide ions.

U.S. Pat. Nos. 2,706,701, 3,028,300, 4,038,476, 4,130,640, 4,214,059, 4,320,114, 4,427,631 and 4,526,751 all describe methods of preparing povidone iodine compositions. None, however, provide solutions to the problems of instability, reliability and reproducibility faced by the present inventors. Furthermore, the importance of the stability of free, equilibrium iodine levels, especially in pharmaceutical terms, is not discussed.

For a full and proper understanding of the present invention, it is important to distinguish in the present preparations between free, equilibrium iodine (the concentration of which may be measured potentiometrically) and available iodine (the concentration of which may be measured by titration).

Povidone iodine solutions contain non-complexed, otherwise known as free, equilibrium iodine, and complexed iodine, in which the iodine is complexed with povidone. The combination of complexed and free iodine constitutes available (titratable) iodine.

For antiseptic/disinfectant purposes it is the level of free, equilibrium iodine (not available iodine) that determines the bactericidal properties of povidone iodine. The higher the level of free iodine, the better the bactericidal effect within a given time span. Of course, the level of free iodine must not become too high, otherwise the unwanted, side-effects of free iodine will become apparent.

Thus it is the aim of the present invention to provide a povidone iodine preparation having a narrowly defined and stable level of free iodine.

By contrast, Winicov in U.S. Pat. No. 4,271,149 is concerned with the stability of available iodine levels. The stability of free iodine levels is not addressed nor is the pharmaceutical importance of these (free iodine) levels. As will be seen in the experimental section of the present specification, the free iodine levels of Winicov's preparations are not stable.

SUMMARY OF THE INVENTION

It is accordingly a primary object of the present invention to produce an iodophor preparation which avoids all of the disadvantages of known preparations, and which particularly provides a predictable microbicidal activity over a prolonged period of time.

It is another object of the present invention to provide the method of producing such a preparation.

It is yet a further object of the present invention to provide an iodophor preparation which contains predetermined quantities of free, equilibrium iodine and which, due to the presence of such free iodine, provides predictable microbicidal effectiveness over a prolonged period of time.

With the above and other objects in view, the present invention mainly comprises a pharmaceutical iodophor preparation having predictable microbicidal effectiveness and long duration of action comprising polyvinylpyrrolidone-iodine (PVPI), free iodine, a source of iodide ions and, as an oxidizing agent, a source of iodate ions, the preparation having a ratio of available (titratable) iodine to iodide between 2:1 and 10:1, a pH between 5 and 6 and a free iodine concentration between 2 and 20 ppm, wherein the amount of iodate ion in the preparation is sufficient to maintain the free iodine concentration between 2 and 20 ppm for at least 12 months at 20° C.

Preferably the ratio of available iodine to iodide is between 2:1 and 6:1, especially between 2:1 and 3.6:1. The pH of the solution is maintained between 5 and 6 by means of a buffer. Preferably the total amount of iodate ions added to the present preparation is between 0.22 and 15% by wt of the preparation.

The free iodine levels of the preparation of the present invention are adjusted to be between 2-20 ppm, depending upon the use for which the preparation is to be put. The lower levels of free iodine are used for the treatment of living beings whereas higher levels of free iodine are used for the treatment of inanimate objects.

The essential features of the present iodophor preparation are the available (titratable) iodine to iodide ratio, described subsequently also as internal ratio, and the free, non-complex-bound, equilibrium iodine content resulting therefrom and from the large quantity of iodate ions, which provides a predictable microbicidal effectiveness and duration of effectiveness. Thus, compared to prior iodophor preparations, it is possible to achieve a higher, stable free iodine content, whilst the available (titratable) iodine content is approximately comparable (to the prior art) and the iodide content is largely constant in relation to the available iodine content.

The advantages offered by the present preparations are outstanding. A predictable, quicker microbicidal effect, compared with previous preparations, and a substantially increased sporocidal effect. Unusually short reaction times of approximately 15 seconds are achieved for the microbicidal effectiveness.

The total iodine content (available iodine plus iodide ion) of the present preparation is preferably 12 to 15 per cent by weight of the polymer weight whilst the available (titratable) iodine content is preferably 9 to 12 per cent by weight of the polymer weight. In a particularly preferred embodiment of the present preparation, the weight ratio of polymer to available iodine is 8.5 to 1. It is additionally preferred that the oxidizing agent (iodate ion) is added in a total quantity of 0.22 to 15, in particular 2 to 8, per cent by weight of the preparation. With this arrangement the preferred oxidizing agent is potassium iodate. It should be noted that the amount of oxidizing agent rises within the above mentioned limits the more the preparation is diluted. Preferably the preparation contains citric acid (to buffer the pH-value) which may be mixed with a sodium phosphate preferably secondary sodium phosphate for higher pH-values.

It was found that the preparation preferably has a free, non-complex-bound, equilibrium iodine content in solution of 2 to 20 ppm $I_2$, preferably 2.5–3.6 ppm $I_2$, for weaker action, or 5–6 ppm $I_2$, for stronger action, the concentration being measured by the potentiometric method of Gottardi (Fresenius Z Anal chem (1983), 582 to 585).

In the German Federal Republic chemical disinfection processes are tested and evaluated according to guidelines of the German Society for Hygiene and Microbiology (see Guidelines for the Testing and Evaluating of chemical disinfection processes, issued Jan. 1, 1981, printed in ISBN 3-437-10716-X). Using the in-vitro tests (quantitative suspension experiments) mentioned in that document it was found that, within a specified time, a direct correlation existed between the free, non-complex-bound, equilibrium iodine content of a preparation and the bactericidal activity of the preparation, when measured according to the guidelines.

In a further preferred feature of the present invention, the preparation exists as a 0.1 to 10 per cent, by weight, PVP iodine solution in water or an alcoholic solution or as a liquid soap, ointment, gel, suppository or oral antiseptic with a 0.1 to 10 per cent by weight PVP iodine content. Accordingly the preferred application of the preparation according to the invention is as a microbicide such as a solution, liquid soap, ointment, gel, suppository, antiseptic, dressing, medicated dressing etc.

Manufacture of the preparations according to the invention may be effected in two ways, i.e. either by preparing a new fresh concentrate or by reprocessing old preparations, in particular an old solution which no longer meets the practical requirements. Accordingly one may proceed by either (a) dissolving the polymer in a polar carrier such as water and/or alcohol, then adding thoroughly dispersed iodine, possibly as a solution, while stirring at a moderately raised temperature, generally below 100° C., and permitting reaction to occur. A check is kept on the progress of the reaction by continuously analyzing the available iodine to iodide ratio. The iodine to iodide ratio is adjusted to have free iodine present for the desired killing effect. As indicated above, the preferred ratio of available iodine to iodide for this purpose is 2:1–10:1, preferably 2:1–6:1, and most preferably 2.1:1 to 3.6:1. This ratio is adjusted by adding iodate ions, while the solution is still at acid pH, in an amount of 0.01–0.45%, preferably 0.02–0.25% by weight. The solution is then analysed to check the amount of free iodine. The amount of free iodine in the solution should be from about 2–20 ppm preferably 2–10 ppm. The amount of free iodine for weaker solutions is preferably between 2.5–3 ppm, and for stronger solutions preferably 5–6 ppm.

The pH of the solution is then increased to between 5 and 6, and preferably between 5.5–5.9, after which iodate ions are added, preferably in an amount of at least 0.2% by wt. of the preparation, to stabilise the free iodine level. The carrier can then be removed by spray-drying or freeze-drying or precipitation if temporary storage is required.

By this process the preparation is produced with a known, predetermined level of free iodine. The preparation is therefore stable from the outset and can be sold immediately, especially for pharmaceutical use. By contrast, preparations prepared simply by mixing the ingredients (in the manner of U.S. Pat. No. 4,271,149, Winicov) take 1-3 months to form a stable level of free iodine and therefore cannot be sold for pharmaceutical purposes until such stabilisation occurs.

As an alternative to the above procedure, one may proceed by (b) Reprocessing an existing iodophor preparation or a dissolved concentrate that does not correspond to the present available iodine to iodide ratio by altering the available iodine to iodide ratio through the addition of iodate ion and constantly checking it analytically, and/or by determining the free non-complex-bound elementary iodine content, until the specified values have been obtained, whereupon the pH-value is adjusted using citric acid and sodium hydroxide if necessary, and adding further iodate ion, whereupon auxiliary substances, diluting agents, etc. are added, if necessary, in order to give the preparation the desired galenic form.

It is thus possible to produce, as required, a solid concentrate as an intermediate product, or an aqueous solution, which may be used undiluted or without further galenic processing, or a galenic preparation such as a solution etc., whereby it is up to the expert to add auxiliary substances and additives according to the requirement and objective.

DESCRIPTION OF THE PREFERRED EMBODIMENTS

The following examples are given to further illustrate the present invention. The scope of the invention is not, however meant to be limited to the specific details of the Examples:

CONTROL EXAMPLE A (RAW MATERIAL)

In a glass or stainless steel flask equipped with stirrer prepare a solution made up of 100 g polyvinylpyrrolidone K 30 (Povidone K30) and 1000 ml distilled water (acidified to a pH below 4). While stirring add 15.26 g potassium iodide. When this is dissolved add potassium iodate in small portions. 3.93 g potassium iodate is required for the complete removal of the iodide ions and the formation of Povidone iodine. Keep stirring until the test for iodide ions is negative.

After stirring for approximately one hour at room temperature the reaction will have stabilised. The solution is then left to stand overnight without stirring.

Now the carrier is extracted under reduced pressure. The Povidone iodine obtained is in the form of a brown-red, free-flowing powder; titratable iodine content approximately 10%, nitrogen content approximately 10.5%. The Povidone iodine obtained in this way fully meets the existing requirements of USP.

CONTROL EXAMPLE B (RAW MATERIAL)

In a glass or stainless steel flask equipped with stirrer prepare a solution made up from 100 g Povidone K 30 and 1000 ml distilled water. While stirring add 15 g finely dispersed iodine in small portions. Stir for a further six hours at room temperature until the iodine is completely dissolved.

When the reaction has stabilized the solution is left to stand overnight without stirring.

Now the carrier is extracted under reduced pressure. The Povidone iodine obtained is in the form of a brown-red, free-flowing powder; titratable iodine content approximately 10%, nitrogen content approximately 10.5%. The Povidone iodine obtained in this way fully meets the existing requirements of USP.

CONTROL EXAMPLE C (RAW MATERIAL)

Instead of Povidone K 30, Povidone K 90 may be used in the control examples A and B. If in all other respects one proceeds as stated, Povidone iodine is obtained, which differs, not in its anti-microbial effectiveness, but in its properties as regards solubility in aqueous carriers, from the products described above.

CONTROL EXAMPLE D (RAW MATERIAL)

Instead of Povidone K 30, Povidone K 17 may be used in the control examples A and B. If in all other respects one proceeds as stated, Povidone iodine is obtained, which differs, not in its anti-microbial effectiveness, but in its properties as regards solubility in aqueous carriers, from the products described above.

EXAMPLE 1

(Preparations with differing iodine to iodide ratio)

Eight different PVP iodine preparations with differing iodine to iodide ratios were manufactured as follows: Batch 1-4; 10 g of PVP iodine containing 10% iodine were dissolved in 100 ml water at room temperature while stirring. Dependent upon the objective the desired iodine to iodide ratio was set up by the addition of potassium iodate as oxidising agent or by potassium iodide. Then the pH value was adjusted by the addition of citric acid and sodium hydroxide. The individual batches had the following parameters:

| Batch | Titratable Iodine | PVP Content | Iodide Content | $I_2$:Iodide |
|---|---|---|---|---|
| 1 | 1.00% | 8.5% | 0.25% | 3.6:1 |
| 2 | 1.00% | 8.5% | 0.33% | 3.0:1 |
| 3 | 1.00% | 8.5% | 0.50% | 2.0:1 |
| 4 | 1.00% | 8.5% | 1.00% | 1.0:1 |

Batch 5-10: 5 g of PVP iodine containing 10% iodine were dissolved in 100 ml water at room temperature while stirring. Dependent upon the objective the desired iodine to iodide ratio was set up by the addition of potassium iodate as oxidising agent or by potassium iodide. Then the pH value was adjusted by the addition of citric acid or sodium hydroxide. The individual batches had the following parameters:

| Batch | Titratable Iodine | PVP Content | Iodide Content | $I_2$:Iodide |
|---|---|---|---|---|
| 5 | 0.50% | 4.25% | 0.125% | 3.6:1 |
| 6 | 0.50% | 4.25% | 0.16% | 3.0:1 |
| 7 | 0.50% | 4.25% | 0.25% | 2.0:1 |
| 8 | 0.50% | 4.25% | 0.50% | 1.0:1 |

A microbiological test was then carried out which revealed that preparations with an iodine to iodide ratio from approximately 3.0:1 are rapidly effective for practical use.

EXAMPLE 2

(Preparation with defined iodine to iodide ratio)

100 ml of a one year old 10% solution of Povidone iodine in water coining 1.0 g titratable iodine and 0.5 g iodide (iodine to iodide ratio=2:1) are adjusted to a pH value of 2 and 0.056 g potassium iodate are added while stirring lightly. After approximately two hours the oxidation reaction has finished. A solution with 1.2 g titratable iodine and 0.34 g iodide has formed, giving in a 3.5:1 iodine to iodide ratio. The solution is adjusted to a pH value of 5.0 to 5.5 and stabilized by the addition of 0.2 g potassium iodate. It shows an excellent anti-microbial effectiveness.

EXAMPLE 3

(Preparation, with a defined free iodine level)

10 g PVP iodine containing 10% iodine were dissolved in 100 ml water at room temperature while stirring. Depending upon the objective a desired free iodine content of 5 ppm was obtained by the addition of potassium iodate as oxidation agent. Then the pH value was raised to 5.0–5.5 by the addition of citric acid and soda lye and the solution was stabilised by the addition of 0.2 g potassium iodate. The solution has an excellent anti-microbial effectiveness.

EXAMPLE 4

(Preparation, stability over time)

The solution manufactured as per example 3 (batch 9) was observed as regards stability of some relevant parameters (pH value, free iodine content, available iodine content) over a period of 12 months and compared with a conventionally prepared preparation (batch 10). As the table shows, the solution manufactured by the new method has an excellent and substantially improved stability within the measured tolerance.

| Batch | Storage period (months) | Available iodine % | Free Iodine (ppm) | pH |
|---|---|---|---|---|
| 9 | 0 | 1.04 | 4.8 | 5.5 |
|   | 3 | 1.04 | 4.9 | 5.5 |
|   | 6 | 1.05 | 5.2 | 5.6 |
|   | 9 | 1.05 | 4.9 | 5.5 |
|   | 12 | 1.06 | 5.1 | 5.6 |
| 10 | 0 | 1.00 | 2.2 | 5.5 |
|   | 3 | 0.98 | 2.0 | 5.2 |
|   | 6 | 0.94 | 1.9 | 4.9 |
|   | 9 | 0.91 | 1.5 | 4.6 |
|   | 12 | 0.90 | 1.3 | 4.2 |

EXAMPLE 5

(Preparation, internal ratio/reduction factors)

According to the "Guideline for the Testing and Evaluating of Chemical Disinfection Processes" by the German Society for Hygiene and Microbiology (DGHM) (Issue 1.1.1981) the bactericidal effect, given as reduction factor, of various batches of 10% aqueous PVP iodine solutions with a titratable iodine to iodide ratio of 3.6:1 or 3:1 and a total of 0.22% by wt iodate added was determined in a quantitative suspension experiment.

N.B. A small proportion of the iodate (ca. 10% of the iodate added) will be consumed during the formation of free iodine.

(a) 3.6:1 ratio

| Batch | Reduction factors RF at | | | |
|---|---|---|---|---|
|   | 30" | 1' | 2' | 5' |
| a | 4.78 | 5.25 | 5.95 | $\geq 7.25$ |
| b | $\geq 7.19$ | $\geq 7.19$ | $\geq 7.19$ | $\geq 7.19$ |
| c | 6.55 | 5.57 | 6.07 | $\geq 7.37$ |
| d | 5.38 | 6.38 | $\geq 7.38$ | $\geq 7.38$ |

(b) 3:1 ratio

| Batch | Reduction factors RF at | | | |
|---|---|---|---|---|
|   | 30" | 1' | 2' | 5' |
| e | 1.48 | 2.72 | 6.59 | $\geq 7.59$ |
| f | 2.48 | 5.67 | 6.0 | $\geq 7.14$ |
| g | 1.34 | 3.06 | 5.14 | $\geq 7.14$ |
| h | 1.09 | 4.43 | $\geq 7.13$ | $\geq 7.13$ |

EXAMPLE 6

(Preparation, free $I_2$ content/reduction factors)

By the process of example 1 eight different batches with internal iodine to iodide ratios of 2.0:1 to 3.6:1 were manufactured. Of these batches i, (see below) was a 5% PVP iodine solution; all other batches were 10% PVP iodine solutions; with the exception of batch (i) all batches were stabilised with potassium iodate. In order to establish the correlation between microbicidal speed of effect and free elementary iodine content, the batches, differing in age, were microbiologically tested over the same period in a quantitative suspension experiment according to the DGHM method and their free elementary iodine content determined by the potentiometric method of Gottardi. The results of these tests are expressed in terms of the reduction factors set out below.

| Batch | Reduction factors RF at | | | ppm $I_2$ | $I_2$:iodide |
|---|---|---|---|---|---|
|   | 30" | 1' | 2' | | |
| i | 0.94 | 1.15 | 2.18 | 1.91 | 2.0:1 |
| j | 4.97 | $\geq 7.50$ | $\geq 7.50$ | 4.97 | 2.4:1 |
| k | 5.31 | $\geq 7.17$ | $\geq 7.17$ | 4.90 | 3.0:1 |
| l | $\geq 7.50$ | $\geq 7.50$ | $\geq 7.50$ | 5.80 | 3.0:1 |
| m | $\geq 7.50$ | $\geq 7.50$ | $\geq 7.50$ | 6.39 | 3.0:1 |
| n | $\geq 7.21$ | $\geq 7.21$ | $\geq 7.21$ | 6.46 | 3.0:1 |
| o | $\geq 7.50$ | $\geq 7.50$ | $\geq 7.50$ | 12.70 | 3.6:1 |
| p | $\geq 7.41$ | $\geq 7.41$ | $\geq 7.41$ | 16.01 | 3.6:1 |

These values show a distinct correlation between ppm $I_2$ and the RF. It is thus possible to control the desired sterilisation times by means of free $I_2$ concentration or internal ratio (available iodine to iodide ratio).

Based on these results stable batches of a 10% PVP iodine solution were manufactured, which easily reached the time value of 2 minutes, previously critical for conventional PVP iodine solutions, at the level of the minimum required reduction factor in the quantitative suspension test against staphylococcus aureus by the DGHM method, even in the concentrated solution.

| Batch | Reduction factors RF at | | | ppm $I_2$ | $I_2$:iodine | pH |
|---|---|---|---|---|---|---|
|   | 30" | 1' | 2' | | | |
| r | 2.26 | 4.40 | $\geq 8.30$ | 4.35 | 2.4:1 | 5.9 |
| s | 3.16 | 5.17 | $\geq 7.91$ | 4.50 | 2.4:1 | 5.9 |

While the invention has been described with respect to particular iodophor preparations containing free iodine, it is to be understood that variations and modifications of the invention can be made.

In order to compare preparations according to the present invention with those described in U.S. Pat. No. 4,271,149 (Winicov), the following compositions were prepared.

EXAMPLE 6

Povidone iodine (K-30) was dissolved in an aqueous glycerol solution. The concentration of free iodine in the solution was then adjusted to between 2.5 and 3.0 ppm by the consecutive addition of appropriate quantities of potassium iodate, citric acid solution and disodium hydrogen phosphate solution.

A nonoxynol solution (Antarox CO 630, Trade Mark) was then added, after which the pH of the solution was adjusted to between pH 5.3 and 5.5 by the addition of aq. sodium hydroxide.

Finally, potassium iodate was added to the solution to stabilise the free iodine concentration and the pH was adjusted to between pH 5.8 and 5.9.

The composition had the following formulation,

|  | %, by wt. |
|---|---|
| Povidone iodine (K-30) | 10.0 |
| (containing povidone, iodine and iodide in a ratio 8.5, 1.0, 0.5) | |
| Glycerol | 1.0 |
| Antarox CO 630 | 0.25 |
| Anhydrous Citric Acid | 0.38 |
| Anhydrous Disodium Hydrogen Phosphate | 0.82 |
| Potassium Iodate | 0.2 |
| Sodium Hydroxide | q.s. for pH adjustment |
| Purified Water | to 100 |

COMPARATIVE EXAMPLE I

A solution according to U.S. Pat. No. 4,271,149, Table III B, was prepared as described in U.S. Pat. No. 4,271,149. The solution had the following formulation,

|  | %, by wt |
|---|---|
| Pluronic P85 | 9.56 |
| Citric Acid | 0.5 |
| Iodine | 1.0 |
| Iodide | 0.445 |
| (equivalent to hydrogen iodide, 0.45%) | |
| Iodate | 0.18 |
| (equivalent to sodium iodate, 0.2%) | |
| Glycerine | 10.0 |
| Sodium Hydroxide | q.s. pH 5.8 |
| Water | to 100 |

COMPARATIVE EXAMPLE II

A solution as described in Comparative Example I was prepared, except that Pluronic P85 was replaced by povidone iodine (K-30).

COMPARATIVE EXAMPLE III

A solution according to U.S. Pat. No. 4,271,149, Table III D, was prepared as described in U.S. Pat. No. 4,271,149. The solution had the following formulation,

|  | %, by wt. |
|---|---|
| Pluronic P85 | 9.56 |
| Citric Acid | 0.5 |
| Iodine | 0.5 |
| Iodide | 0.198 |
| (equivalent to hydrogen iodide, 0.2%) | |
| Iodate | 0.18 |
| (equivalent to sodium iodate, 0.2%) | |
| Glycerine | 10.0 |
| Sodium Hydroxide | q.s. pH 5.6 |
| Water | to 100 |

COMPARATIVE EXAMPLE IV

A solution according to Comparative Example III was prepared, except the Pluronic P85 was replaced by povidone iodine (K-30).

COMPARATIVE EXAMPLE V

A solution according to U.S. Pat. No. 4,271,149, Table III F, was prepared as described in U.S. Pat. No. 4,271,149. The solution had the following formulation,

|  | %, by wt. |
|---|---|
| Pluronic P85 | 9.56 |
| Citric Acid | 0.5 |
| Iodine | 0.25 |
| Iodide | 0.099 |
| (equivalent to hydrogen iodide, 0.1%) | |
| Iodate | 0.18 |
| (equivalent to sodium iodate, 0.2%) | |
| Glycerine | 10.0 |
| Sodium Hydroxide | q.s. pH 5.6 |
| Water | to 100 |

COMPARATIVE EXAMPLE VI

A solution according to Comparative Example V was prepared except that Pluronic P85 was replaced by povidone iodine (K-30).

COMPARATIVE EXAMPLE VII

A solution according to U.S. Pat. No. 4,271,149, Table III H, was prepared as described in U.S. Pat. No. 4,271,149. The solution had the following formulation,

|  | %, by wt. |
|---|---|
| Pluronic P85 | 9.56 |
| Citric Acid | 0.5 |
| Iodine | 0.1 |
| Iodide | 0.0395 |
| (equivalent to hydrogen iodide, 0.04%) | |
| Iodate | 0.045 |
| (equivalent to sodium iodate, 0.05%) | |
| Glycerine | 10.0 |
| Sodium Hydroxide | q.s. to 5.0 |

COMPARATIVE EXAMPLE VIII

A solution according to Comparative Example VII was prepared except that Pluronic P85 was replaced by povidone iodine (K-30).

The stability of the preparation of Example 6 was then compared with the stability of the preparations of Comparative Examples I to VIII. All of the samples were kept at 37° C. and both the available iodine and free iodine levels in the samples were measured periodically. Results are shown in Table 1.

| Example | Time (months) | Available Iodine (% by wt) | Free Iodine (ppm) |
|---|---|---|---|
| 6 | 1 | 1.04 | 2.24 |
|  | 4 | 1.06 | 2.38 |
|  | 6 | 1.06 | 2.41 |
|  | 9 | 1.08 | 2.40 |

-continued

| Example | Time (months) | Available Iodine (% by wt) | Free Iodine (ppm) |
|---|---|---|---|
|  | 12 | 1.10 | 2.33 |
| I | 0.5 | 1.08 | 1.5 |
| US 4271149 Table III B Pluronic P85 | 1 | 1.08 | 0.9 |
| II | 0.5 | 0.96 | 1.28 |
| US 4271149 Table III B Povidone K-30 | 1.5 | 0.96 | 1.19 |
|  |  | 0.97 | 0.86 |
| III | 0.5 | 0.48 | 1.63 |
| US 4271149 Table III D Pluronic P85 | 1 | 0.48 | 0.79 |
| IV | 0.5 | 0.45 | 1.09 |
| US 4271149 Table III D Povidone K-30 | 1 | 0.46 | 0.86 |
| V | 0.5 | 0.23 | 0.75 |
| US 4271149 Table III F Pluronic P85 | 1 | 0.23 | 0.40 |
| VI | 0.5 | 0.20 | 0.80 |
| US 4271149 Table III F Povidone K-30 | 1 | 0.22 | 0.56 |
| VII | 0.5 | 0.094 | 0.25 |
| US 4271149 Table III H Pluronic P85 | 1 | 0.1 | 0.17 |
| VIII | 0.5 | 0 | 0.003 |
| US 4271149 Table III H Povidone K-30 | 1 | 0 | 0 |

It will be noted that in the preparation of the present invention (Example 6), both the available iodine and free iodine levels were stable for 12 months (at least). By contrast, in the case of the preparations of U.S. Pat. No. 4,271,149 (Examples I to VIII), the available iodine level remained constant, but the free iodine concentration dropped dramatically after just 1 month. As it is the free iodine level that determines the therapeutic effectiveness of an iodophor preparation, the advantage of the present preparations over those of U.S. Pat. No. 4,271,149 can immediately be seen.

The advantage offered by the preferred method of preparing the present preparation is illustrated below. The available iodine and free iodine concentrations, over a period of time at 20° C., of a preparation produced according to Example 6 was compared with those of a preparation having the same composition but produced simply by mixing the constituents (Example 7). Results are given in Table 2.

TABLE 2

| Example | Time (months) | Available Iodine (% by wt) | Free Iodine (ppm) |
|---|---|---|---|
| 6 | 0 | 1.00 | 2.45 |
|  | 1 | 1.02 | 2.47 |
|  | 2 | 1.04 | 2.58 |
|  | 3 | 1.05 | 2.43 |
| 7 | 0 | 1.03 | 1.20 |
|  | 1 | 1.04 | 1.75 |

TABLE 2-continued

| Example | Time (months) | Available Iodine (% by wt) | Free Iodine (ppm) |
|---|---|---|---|
|  | 2 | 1.06 | 2.08 |
|  | 3 | 1.06 | 2.16 |

It can be seen that by using the preferred process of this invention (Example 6), namely, (a) treating PVPI and iodide ion in acidic solution with iodate ion to give an acidic solution containing 2-20 ppm free iodine and having an available iodine to iodide ratio of between 2:1 and 10:1, (b) increasing the pH of the solution to between 5 and 6, and, (c) stabilising the free iodine concentration by adding additional iodate ion, the required level of free iodine is achieved immediately and remains constant.

By contrast, simply by mixing the ingredients to give the same composition (Example 7), a stable level of free iodine takes about 2 months to achieve.

In industrial/pharmaceutical terms, the advantages offered by the preferred process of this invention are clear.

We claim:

1. A method of producing a povidone iodine preparation having a predetermined concentration of free iodine which is immediately achieved and which remains constant and having predictable microbicidal effectiveness and long duration of action, the method comprising the steps of treating a mixture of povidone iodine and iodine ion in acidic solution with iodate ion to form an acidic solution containing between 2 and 20 ppm of free iodine and having an a available iodine to iodide ratio between 2:1 and 10:1, increasing the pH of said acidic solution to between 5 and 6, and adding additional iodate ion to the thus formed solution in an amount sufficient to maintain the amount of free iodine therein at a concentration of between 2 and 20 ppm, whereby the free iodine concentration is immediately achieved and remains stable for at least 12 months at 20° C.

2. A method according to claim 1 wherein the total amount of iodate ion added is between 0.22 wt % and 15 wt % of the preparation.

3. The method of claim 1 wherein the iodide ions are supplied by potassium iodide and the iodate ions are supplied by potassium iodate.

4. The method of claim 1 wherein the available iodine to iodide ratio is between 2:1 and 6:1.

5. The method of claim 1 wherein the available iodine to iodide ratio is between 2.1:1 and 3.6:1.

6. The method of claim 1 wherein the amount of iodate ion added is sufficient to maintain the concentration of free iodine at between 2-10 ppm.

7. The method of claim 1 wherein the amount of iodate ion is sufficient to maintain the free iodine concentration at between 2.5-3 ppm.

8. The method of claim 1 wherein the amount of iodate ion added is sufficient to maintain the concentration of free iodine at between 5-6 ppm.

9. The method of claim 1 wherein the pH of said acidic solution is increased to between 5.5-5.9.

* * * * *